United States Patent
Itoh et al.

(10) Patent No.: US 7,968,098 B2
(45) Date of Patent: Jun. 28, 2011

(54) HLA-A24-BINDING KIF-DERIVED PEPTIDE

(75) Inventors: Kyogo Itoh, Kurume (JP); Ryuya Yamanaka, Kurume (JP); Mamoru Harada, Fukuoka (JP)

(73) Assignee: Kurume University, Fukuoka (JP)

( * ) Notice: Subject to any disclaimer, the term of this patent is extended or adjusted under 35 U.S.C. 154(b) by 248 days.

(21) Appl. No.: 12/309,950

(22) PCT Filed: Aug. 3, 2007

(86) PCT No.: PCT/JP2007/065273
§ 371 (c)(1),
(2), (4) Date: Feb. 4, 2009

(87) PCT Pub. No.: WO2008/016141
PCT Pub. Date: Feb. 7, 2008

(65) Prior Publication Data
US 2010/0074912 A1    Mar. 25, 2010

(30) Foreign Application Priority Data
Aug. 4, 2006    (JP) ................................ 2006-213398

(51) Int. Cl.
*A61K 38/04*    (2006.01)
(52) U.S. Cl. ..... 424/185.1; 530/328; 514/15; 424/277.1; 424/93.1; 435/372

(58) Field of Classification Search .................. 530/328; 514/15; 424/185.1, 277.1, 93.1; 435/372
See application file for complete search history.

(56) References Cited

FOREIGN PATENT DOCUMENTS

| WO | 03/037917 | 5/2003 |
|----|-----------|--------|
| WO | 2004/018680 | 3/2004 |

OTHER PUBLICATIONS

S. Shichijo et al., "A unique gene having homology with the kinesin family member 18A encodes a tumour-associated antigen recognised by cytotoxic T lymphocytes from HLA-A2+ colon cancer patients", European Journal of Cancer, vol. 41, pp. 1323-1330, 2005.

M. Harada et al., "Kinesin superfamily protein-derived peptides with the ability to induce glioma-reactive cytotoxic T lymphocytes in human leukocyte antigen-A24+ glioma patients", Oncology Reports, vol. 17, pp. 629-636, 2007.

*Primary Examiner* — Stephen Rawlings
(74) *Attorney, Agent, or Firm* — Wenderoth, Lind & Ponack, L.L.P.

(57) ABSTRACT

An object of the invention is to provide a peptide derived from a glioma-associated antigen being useful for the specific immunotherapy for glioma patients. The invention provides a KIF-derived peptide which is capable of binding to an HLA-A24 molecule and recognized by the cellular immune system, and a pharmaceutical composition comprising said peptide for the treatment or prevention of glioma.

8 Claims, 3 Drawing Sheets

HLA-A24-BINDING KIF-DERIVED PEPTIDE

This application is a U.S. national stage of International Application No. PCT/JP2007/065273 filed Aug. 3, 2007.

FIELD OF THE INVENTION

The present invention relates to KIF-derived peptides which are useful for the specific immunotherapy for HLA-A24 positive glioma patients.

BACKGROUND OF THE INVENTION

There has been little improvement in the prognosis and survival of malignant glioma patients over the past decade (Non-Patent Literatures 1 and 2), despite the fact that aggressive combined treatment modalities have been developed. Therefore, the development of a new treatment modality is needed, and one option is specific immunotherapy. Recent advances in tumor immunology have led to the discovery of several cancer-associated antigens and their epitope peptides that can be recognized by cytotoxic T lymphocytes (CTLs) (Non-Patent Literature 3). Glioma-associated antigens and their peptides have also been reported (Non-Patent Literatures 4-6), but their numbers are very limited.

[Non-Patent Literature 1] Karpeh M S, Kelsen D P, Tepper J E (2001) Cancer of the stomach. In: Devita V T Jr. editor. Cancer: principles & practice of oncology. 6th ed. Philadelphia: Lippincott Williams & Wilkins; p. 1092-1121
[Non-Patent Literature 2] Stewart L A (2002) Chemotherapy in adult high-grade glioma: s systematic review and meta-analysis of individual patient data from 12 randomized trials. Lancet 359: 1011-1018
[Non-Patent Literature 3] Renkvist N, Castelli C, Robbins P F, Parmiani G (2001) A listing of human tumor antigens recognized by T cells. Cancer Immuno Immunother 50: 3-15
[Non-Patent Literature 4] Liu G, Ying H, Zeng G, Wheeler C J, Black K L, Yu J S (2004) HER-2, gp100, and MAGE-1 are expressed in human glioblastoma and recognized by cytotoxic T cells. Cancer Res 64: 4980-4986
[Non-Patent Literature 5] Murayama K, Kobayashi T, Imaizumi T, Mastunaga K, Kurimoto T, Shigemori M, Shichijo S, Itoh K (2000) Expression of the SART3 tumor-rejection antigen in brain tumors and induction of cytotoxic T lymphocytes by its peptides. J Immunother 23: 511-518
[Non-Patent Literature 6] Tsuda N, Nonaka Y, Shichijo S, Yamada A, Ito M, Maeda Y, Harada M, Kamura T, Itoh K (2002) UDP-Gal: bGlcNAc b1, 3-galactosyltransferase, polypeptide 3 (GALT3) is a tumour antigen recognized by HLA-A2-restricted cytotoxic T lymphocytes from patients with brain tumour. Br J Cancer 87: 1006-1012

DISCLOSURE OF THE INVENTION

Problem to Be Solved By the Invention

An object of the present invention is to provide a peptide derived from a glioma-associated antigen which is useful for the specific immunotherapy for glioma patients.

Means for Solving the Problem

The present invention provides a KIF-derived peptide which is capable of binding to an HLA-A24 molecule and recognized by the cellular immune system. Particularly, the present invention provides a peptide consisting of the amino acid sequence of SEQ ID No: 3 or 15 or a peptide derivative thereof. Further, the present invention also provides a nucleic acid molecule which encodes the peptide or peptide derivative of the present invention and a vector comprising the nucleic acid molecule.

The present invention further provides a pharmaceutical composition, especially provides the composition of cancer vaccine, for the treatment or prevention of glioma comprising the peptide, peptide derivative or vector of the present invention.

The present invention further provides a method for inducing a glioma-reactive cytotoxic T lymphocyte, which comprises contacting peripheral blood mononuclear cells (PBMCs) collected from an HLA-A24 positive (HLA-A24$^+$) glioma patient with the peptide or peptide derivative of the present invention.

Furthermore, the present invention provides a method for preparing, an antigen presenting cell on the surface of which a complex between a KIF-derive peptide or a peptide derivative thereof and an HLA-A24 molecule is presented, which comprises introducing the peptide or peptide derivative or the vector of the present invention into a cell having an antigen-presenting ability derived from an HLA-A24$^+$ glioma patient.

The present invention further provides a method for the treatment or prevention of glioma, which comprises administering the peptide, peptide derivative or vector of the present invention, particularly the peptide consisting of the amino acid sequence of SEQ ID NO: 3 or 15 as a cancer vaccine, to a glioma patient.

The present invention also provides use of the peptide, peptide derivative or vector of the present invention for the manufacture of a pharmaceutical composition for the treatment or prevention of glioma, particularly, use of the peptide consisting of the amino acid sequence of SEQ ID No: 3 or 15 for the manufacture of a caner vaccine for the treatment or prevention of glioma.

Effect of the Invention

According to the present invention, KIF-derived peptides which can induce CTLs being capable of killing glioma cells in HLA-A24$^+$ cancer patients are provided. According to the present invention, the specific immunotherapy for HLA-A24$^+$ glioma patients became possible.

BEST MODE FOR CARRYING OUT THE INVENTION

Figure 1:
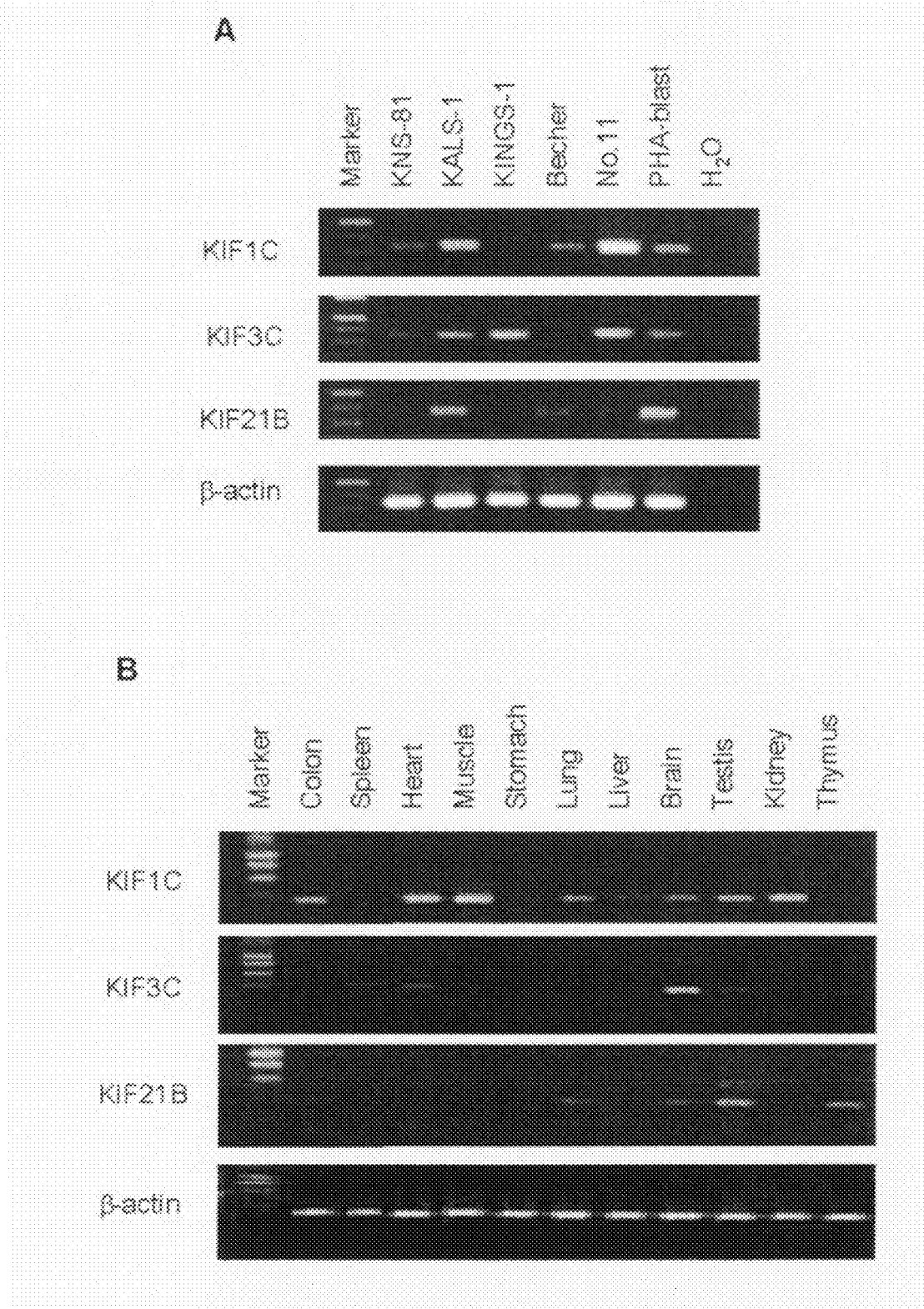
FIG. 1 mRNA expression of three KIF genes in five glioma cell lines (A) and a panel of normal tissues (B). The glioma cell lines tested are as follows: KNS-81 (malignant glioma), KALS-1 (glioblastoma), KINGS-1 (anaplastic astrocytoma), Becher (astrocytoma), and No. 11 (anaplastic astrocytoma). Expression of β-actin was assayed as a control.

In the present invention, "KIF-derived peptide" or "KIF peptide" refers to a peptide fragment consisting of an amino acid sequence which is a part of the amino acid sequence of kinesin superfamily protein KIF1C, KIF3C or KIF21B. The amino acid sequences of KIF1C, KIF3C and KIF21B have been disclosed by GenBank under accession number of NM_006612, NM_002254 and XM_371332, respectively.

According to the invention, the phrase "a peptide is capable of binding to an HLA-A24 molecule" means that said peptide can form a complex with an HLA-A24 molecule to be presented on the cell surface. In general, peptides that are capable of binding to an HLA molecule shares some specific amino acid sequences with regularity depending on the types of the HLA. The specific amino acid sequences with regularity are called as "binding motifs". That is, the binding motif to an HLA-A24 molecule is the sequence wherein the amino acid next to the N-terminal is tyrosine or phenylalanine and that at the C-terminal is isoleucine, leucine or phenylalanine. Binding of a peptide having the HLA-A24 binding motif to an HLA-A24 molecule can be determined using computer analysis such as Bioinformatics and Molecular Analysis Section (NIH, Bethesda, Md.) (Parker K C, Et al., J. Immunol., 152:153-175, 1994).

According to the invention, the phrase "a peptide is recognized by the cellular immune system" means that the peptide is recognized by a specific CTL. In other word, the peptide has an ability to induce a peptide specific CTL. The ability to induce the peptide specific CTL can be examined by, for example, determining whether or not a cytokine such as interferon-γ (IFN-γ) is produced by peptide-stimulated PBMCs in response to antigen presenting cells which are pulsed with said peptide using the ELISA technique or the like. In addition, cytotoxic activity of the induced CTL can be determined by the $^{51}$Cr-release assay and the like. The peptide of the present invention is preferred to have 8 to 14, more preferably 8 to 11 and especially, 9 or 10 amino acid residues in view of good recognition by CTL.

According to the invention, the phrase "a peptide is recognized by the humoral immune system" means that an IgG specific to said peptide is present in the body. That is, the peptide-specific IgG is detected in the plasma of the subject. Peptides recognized by both the cellular and humoral immune systems are expected to exhibit higher immunogenicity and CTL-inducing ability, and therefore, preferable as peptides of the present invention. The amount of the specific IgGs in the plasma can be determined by commonly known ELISA techniques and the like.

A peptide consisting of the amino acid sequence IYCERVRDLL (KIF1C$_{149-158}$, SEQ ID NO: 3) or KYKAMESKL (KIF3C$_{512-520}$, SEQ ID NO: 15) is particularly preferred as a peptide of the invention.

According to the invention, "a peptide derivative of a KIF-derived peptide" is a peptide consisting of the amino acid sequence of the KIF-derived peptide except that substitution, deletion and/or addition of one or two amino acids have been introduced and is capable of binding to an HLA-A24 molecule and recognized by the cellar immune system. Whether or not a peptide derivative has the desired properties can be determined by the above-described procedures.

In order not to alter the property of the original peptide, the substitution of an amino acid is preferably made within the amino acids belonging to the same family, such as polar amino acids, non-polar amino acids, hydrophobic amino acids, hydrophilic amino acids, positively charged amino acids, negatively charged amino acids and aromatic amino acids. The deletion and/or addition of an amino acid are preferably made so that the number of the amino acid residues consisting the derivative is 8-11.

The substitution, deletion and/or addition of an amino acid is preferably made so that the derivative is acceptable in view of an HLA binding motif. That is, the substitution, deletion and/or addition of an amino acid is preferably made so that the amino acid next to the N-terminal is tyrosine or phenylalanine and the C-terminus amino acid is isoleucine, leucine or phenylalanine.

According to the invention, a peptide derivative particularly preferred is a peptide consisting of the amino acid sequence of SEQ ID No: 3 except that the amino acid residue next to the N-terminal is substituted by phenylalanine and/or the C-terminus amino acid residue is substituted by isoleucine or phenylalanine as well as that consisting of the amino acid sequence of SEQ ID No: 15 except that the amino acid residue next to the N-terminal is substituted by phenylalanine and/or the C-terminus amino acid residue is substituted by isoleucine or phenylalanine.

The amino acids constituting the peptides and peptide derivatives according to the invention may be natural amino acids or amino acid analogues. Amino acid analogues may include N-acylated, O-acylated, esterified, acid amidated and alkylated amino acids. The amino or carboxylic group or the like of the amino acid residue constituting the peptide or peptide derivative of the invention may be modified so long as it does not significantly deteriorate the function of the peptide. The modification may be addition of formyl, acetyl or t-butoxycarbonyl group at the N-terminus- or free-amino group, or addition of methyl, ethyl, t-butyl or benzyl group at the C-terminus- or free carboxylic group.

The peptide and peptide derivative according to the present invention may be synthesized by a conventionally used peptide synthesizing procedure. Examples of the conventionally used procedures are those described in the literatures including "Peptide Synthesis", Interscience, New York, 1966; "The Proteins", vol. 2, Academic Press Inc., New York, 1976; "Pepuchido-Gosei", Maruzen. Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

The peptide and peptide derivative of the present invention may be those generated by fragmentation of a polypeptide containing the amino acid sequence of the peptide or peptide derivative of the present invention in a cell. The present invention encompasses the use of such peptide or peptide derivative as above. As long as the peptide or peptide derivative of the present invention can be provided, the polypeptide may comprise any number of amino acid residues and any amino acid sequence.

The present inventors found that KIF1C, KIF3C and KIF21B were highly expressed in tissues of malignant glioma. Glioma is a tumor arisen from glial cells which support neuronal cells. The peptide and peptide derivative of the present invention can effectively induce and increase CTLs specifically killing HLA-A24$^+$ glioma cells and therefore, are useful for treating glioma patients.

The present invention provides a pharmaceutical composition for the treatment or prevention of glioma comprising the peptide or peptide derivative of the present invention. The pharmaceutical composition of the present invention may comprise one peptide or peptide derivative of the present invention, or a combination of two or more peptides and/or peptide derivatives. Since a cancer patient has a mixture of CTLs recognizing a plurality of different cancer antigen peptides, it is effective to use a plurality of the peptides or peptide derivatives of the present invention in combination. The peptide or peptide derivative of the invention may be used in combination with a cancer antigen peptide other than the peptide of the present invention.

The pharmaceutical composition of the present invention may comprise a pharmaceutically acceptable carrier or the like in addition to the peptide or peptide derivative of the present invention. Examples of the carrier may include cellulose, amino acid polymers and albumin. The pharmaceutical composition of the present invention may be formulated as liposomal preparations, particulate preparations in which the ingredient is bound to beads having a diameter of several micro maters, or preparations in which the ingredient is attached to lipids. The pharmaceutical composition of the present invention may be administered along with an adjuvant which has conventionally been used for vaccination in order to establish the immune response effectively. The composition may be administrated intradermally or subcutaneously.

The pharmaceutical composition of the present invention can be used as a cancer vaccine. The dose may be determined based on the condition of the disease to be treated, age and body weight of the respective patient. The amount of the peptide or peptide derivative of the present invention in the pharmaceutical composition may be 0.0001 mg-1000 mg, preferably 0.001 Mg-100 mg, more preferably 0.01 mg-10 mg, even more preferably 0.1-5 or 0.5-3 mg. The pharmaceutical composition may preferably be administered once every several days, several weeks or several months for 1-3 years.

The present application provides a nucleic acid molecule encoding the peptide or peptide derivative of the present invention and a vector comprising said nucleic acid molecule. By introducing the vector comprising the nucleic acid molecule of the invention into an antigen presenting cell, the peptide or peptide derivative of the invention is expressed, and a complex between an HLA molecule and a peptide or peptide derivative of the present invention is presented on the surface of the cell. Thus obtained antigen presenting cell can effectively increase a peptide-specific CTL against glioma cells.

Examples of vectors in which the nucleic acid molecule of the present invention is incorporated may include various plasmid vectors and viral vectors such as adenovirus, adeno-associated virus, retrovirus and vaccinia virus vectors (Liu M, Acres B, Balloul J M, Bizouarne N, Paul S, Slos P, Squiban P. Gene-based vaccines and immunotherapeutics. Proc Natl Acad Sci USA 101 Suppl, 14567-71, 2004). Methods for preparing vectors have been well known in the art (Molecular Cloning: A laboratory manual, 2nd ed. New York, Cold Spring Harbor Laboratory).

The vector of the present invention may be administered to a patient so that the peptide or peptide derivative of the invention is expressed in antigen presenting cells in the body of the patient. Alternatively, the vector is introduced ex vivo in a suitable cell, for example a dendric cell derived from the patient, so that the cell expresses the peptide or peptide derivative of the invention, and then the cell is returned to the patient. Those methods are well known in the art (Hrouda D, Dalgleish A G. Gene therapy for prostate cancer. Gene Ther 3: 845-52, 1996).

The amount of the vector to be administered may vary depending on the condition of the disease to be treated, the age and body weight of the patient to be treated and the like, and may preferably be 0.1 μg-100 mg, more preferably 1 μg-50 mg as an amount of DNA. The vector may be administered, for example, intravenously, subcutaneously, or intradermally.

By the method for inducing a CTL according to the present invention, a CTL which kills HLA-A24+ glioma cells is provided. In the present invention, "glioma-reactive" regarding a CTL refers the property of the CTL which can recognize a complex between a cancer antigen peptide and an HLA molecule on glioma cells and kill the glioma cells. The method of inducing a CTL according to the present invention may be carried out for example by incubating PBMCs collected from an HLA-A24+ glioma patient in vitro in the presence of the peptide or peptide derivative of the present invention. The CTL induced by the present method is useful for the adoptive immunotherapy wherein the induced CTL is returned into the patient from which the PBMCs have been collected to kill cancer cells.

The CTL inducing kit of the present invention can be used for the aforementioned method for inducing a CTL. The kit of the present invention comprises one or more peptides and/or peptide derivatives of the present invention. In addition, the kit may further comprise a suitable buffer, culture media and the like.

By the method for the preparation of an antigen presenting cell of the present invention, an antigen presenting cell which can be used for inducing a CTL against HLA-A24+ glioma cells is provided. The method of the preparation of an antigen presenting cell of the present invention may be carried out, for example, by incubating a cell having an antigen-presenting ability derived from a HLA-A24+ glioma patient with the peptide or peptide derivative of the present invention so that the peptide or peptide derivative is bound to an HLA molecule and presented on the cell surface. Alternatively, a vector which encodes the peptide or peptide derivative of the invention may be introduced into the aforementioned cell such that the peptide or peptide derivative is expressed. The cell having an antigen presenting ability may be, for example, dendritic cell. Dendritic cell derived from a patient can be prepared from PBMCs collected from the patient by separating cells adhered to a culture plate and then incubating the separated cells in the presence of IL-4 and GM-CSF for one week. The antigen presenting cell prepared by the method of the present invention can induce a CTL that specifically recognizes a complex between a peptide or peptide derivative of the present invention and an HLA molecule presented on the surface of the antigen presenting cell. When the antigen presenting cell of the invention is administered to an HLA-A24+ glioma patient, they can induce a glioma-reactive CTL in the body of the patient.

The kit for the preparation of an antigen presenting cell according to the present invention is used for carrying out the aforementioned method of the present invention. The kit of the present invention comprises one or more of the peptides and/or peptide derivatives of the present invention and may further comprise a suitable buffer, culture media and the like.

The present invention further provides a method for treating or preventing glioma, which comprises administering the peptide, peptide derivative, or vector of the invention to a patient in need thereof. In addition, the present invention also provides use of the peptide, peptide derivative or vector of the present invention for the manufacture of a pharmaceutical composition for the treatment or prevention of glioma.

The present invention is further illustrated by the following examples, but is not restricted by these examples in any way.

Examples

1. Materials and Methods 1.1 Samples and cDNA Microarray

Samples were obtained from 52 glioma patients who underwent an operation. The study was approved by the Ethical Committee of Niigata University, and complete written informed consent was obtained from all of the patients. They consisted of 16 grade II cases, 14 grade III cases, and 22 grade IV cases based on the WHO grade classification (Kleihues et al, J Neuropathol Exp Neurol 61: 215-225, 2002). Genetic analysis was performed using Agilent cDNA microarrays (Agilent Technologies, Palo Alto, Calif., USA). Total RNA (20 µg) was reverse transcribed using an Agilent direct-label cDNA synthesis kit (Agilent Technologies) according to the manufacturer's directions. Labeled cDNA was purified using QIAquick PCR Purification columns (Qiagen, Valencia, Calif., USA) and then concentrated by vacuum centrifugation. cDNA was suspended in hybridization buffer, and hybridized to Agilent human 1 cDNA microarrays (Agilent Technologies) for 17 h at 65° C. according to the Agilent protocol. To avoid generation of false between-group differences by randomly pairing glioma samples on the two channel cDNA arrays, each sample was individually labeled, and co-hybridized with a normal brain sample labeled with a complementary dye. Normal brain samples were generated by pooling equal amounts of RNA from each control sample, and labeling as for individual samples. In addition, cyanine dye switch hybridizations were performed for each sample. Normal brain samples were purchased from Clontech (Tokyo, Japan). After chips were washed using 5% SSC/0.1% SDS solution, the fluorescence intensity was measured using laser scanner, and analyzed using Feature Extraction Software (ver. A.4.0.45; Agilent Technologies) according to the manufacturer's instructions. A total of 12,729 genes were analyzed.

1.2 Cell Lines

The glioma cell lines used in this study were as follows: KNS-81 (JCRB Cell Bank, IFO 50359), KALS-1 (JCRB Cell Bank, IFO 50434), KINGS-1 (Department of neurosurgery, Kurume University), Becher, and No. 11 (JCRB Cell Bank, IFO 50369). C1R-A24 is an HLA-A*2402-expressing subline of C1R lymphoma (Dr. M. Takiguchi, Kumamoto University).

1.3 Reverse Transcriptase-Polymerase Chain Reaction (RT-PCR)

Total RNA was isolated from cancer cell lines using RNAzol™ B (Tel-Test Inc., Friendswood, Tex., USA). The cDNA was prepared using the SuperScript™ Preamplification System for First Strand cDNA Synthesis (Invitrogen, Carlsland, Calif.), and was amplified using the following primers:

```
KIF1C     sense      5'-CAAGTGTGTGGTCAGCATGC-3'  (SEQ ID NO: 29)
          anti-sense 5'-CTCTGGTTCTCACTAAGCG-3'   (SEQ ID NO: 30)

KIF3C     sense      5'-TATGATGCCAGCTCCAAGC-3'   (SEQ ID NO: 31)
          anti-sense 5'-ATTCTTGGTGACGAAGGAGG-3'  (SEQ ID NO: 32)

KIF21B    sense      5'-AATGTGATCAGCGCCTTAGG-3'  (SEQ ID NO: 33)
          anti-sense 5'-TGTAGCATGGCATTCTCTCG-3'  (SEQ ID NO: 34)

β-actin   sense      5'-CTTCGCGGGCGACGATGC-3'    (SEQ ID NO: 35)
          anti-sense 5'-CGTACATGGCTGGGGTGTTG-3'  (SEQ ID NO: 36)
```

PCR was performed using TaqDNA polymerase in a DNA thermal cycler (iCycler; Bio-Rad Laboratories, Hercules, Calif., USA) for 30 cycles of 95° C. for 30 sec, 60° C. for 30 sec, and 72° C. for 30 sec. The PCR products were separated by electrophoresis on 2% agarose gel.

1.4 Measurement of Anti-Peptide Antibody

The levels of anti-peptide immunoglobulin G (IgG) were measured by the Luminex™ system as previously reported (Komatsu N et al, Scand J Clin Invest 2004; 64: 1-11). In brief, plasma was incubated with 25 µl of peptide-coupled color-coded beads (Luminex Corp., Austin, Tex., USA) for 2 h at room temperature on a plate shaker. After incubation, the mixture was washed with a vacuum manifold apparatus and incubated with 100 µl of biotinylated goat anti-human IgG (BA-3080, Vector Laboratories, Burlingame, Calif., USA) for 1 h at room temperature. The plate was then washed, and 100 µl of streptavidin-PE (S-866, Molecular Probes, Eugene, Oreg., USA) was added to each well and was incubated for 30 min at room temperature on a plate shaker. The bound beads were washed three times followed by the addition of 100 µl of Tween-PBS to each well. Fifty µl of each sample was then examined using the Luminex™ system.

1.5 Induction of Peptide-Specific CTLs from PBMCs

Peptides with >90% purity were purchased from Hokkaido System Science (Sapporo, Japan). A influenza (Flu) virus-derived peptide (RFYIQMCTEL, SEQ ID NO: 26), EB virus-derived peptide (TYGPVFMCL, SEQ ID NO: 27), and HIV-derived peptide (RYLRQQLLGI, SEQ ID NO: 28) were used as controls binding to HLA-A24 alleles. Assays for the detection of peptide-specific CTLs were performed according to a previously reported method with several modifications (Hida N et al, Cancer Immunol Immunother 2002; 51:219-28). Briefly, PBMCs were incubated with 10 µg/ml of each peptide in quadruplicate in a 96-well microplate (Nunc, Roskilde, Denmark). The culture medium consisted of 45% RPMI 1640, 45% AIM-V medium (Life Technologies, Gaithersburg, Md., USA), 10% FCS, 100 units/ml interleukin (IL)-2, and 0.1 mM MEM nonessential amino acid solution (Life Technologies). On the 15$^{th}$ day of culture, cells were separated into four wells. The cells in two wells were cultured with the corresponding peptide-pulsed C1R-A24 cells, and those in the other two wells were cultured with HIV peptides-pulsed C1R-A24 cells. After an 18-h incubation, the supernatant was collected, and the IFN-γ production was determined by ELISA. The successful induction of peptide-specific CTLs was judged to be positive when the P value was less than 0.05 by the two-tailed Student's t-test and the difference in IFN-γ production compared with the HIV peptide was >100 pg/ml.

1.6 Cytotoxicity Assay

Peptide-stimulated PBMCs were tested for their cytotoxicity against No. 11 (HLA-A24 negative) and KNS-81 (HLA-A24 positive) by a standard 6-h $^{51}$Cr-release assay. Phytohaemagglutinin (PHA)-activated T cells (T cell blast) from HLA-A24 positive healthy donors were used as a negative control. The PBMCs were stimulated with each of the KIF peptides (10 µg/ml) in the presence of IL-2 (100 units/ml) every 3 days for 15 days, followed by incubation with IL-2 alone for an additional 15 days. After CD8$^+$ T cells were positively isolated using a CD8-positive isolation kit (Dynal, Oslo, Norway), 2,000 $^{51}$Cr-labeled cells per well were cultured with effector cells in 96-round-well plates. The specific $^{51}$Cr-release was calculated according to the following formula: % specific lysis=(test sample release−spontaneous release)×100/(maximum release−spontaneous release). Spontaneous release was determined using the supernatant of the sample incubated with no effector cells, and the maximum release was then determined by the supernatant of the sample incubated with 1% Triton X (Wako Pure Chemical Industries, Osaka, Japan). In some experiments, anti-HLA class I (W6/32, mouse IgG2a) (BioLegend, Camino Santa Fe, San Diego, Calif., USA), anti-HLA class II (HLA-DR) (L243, mouse IgG2a) (ATCC #HB-55), and anti-CD14 (JML-H14, mouse IgG2a) (established in Department of Immunology, Kurume University) mAb were added to the wells at the initiation of the culture. The specificity of peptide-stimulated PBMCs was also confirmed by a cold inhibition assay. 20,000 unlabeled C1R-A24 cells, which were pre-pulsed with either the HIV peptide or a corresponding peptide, were used as cold target cells. Unlabeled C1R-A24 cells were added at a hot to cold target ratio of 10 to 1.

2. Results 2.1 mRNA Expression of Three KIF Genes in Glioma and Normal Tissues

Samples obtained from 52 glioma patients were analyzed using an Agilent cDNA microarray. The fluorescence intensity of 36 malignant glioma tissues was compared to those of 16 benign glioma and normal brain tissues. A total of 12,729 genes were analyzed in this manner, and 17 genes were found to be expressed more highly in malignant glioma tissues than in benign glioma and a panel of normal tissues, including the brain, adrenal gland, bone marrow, colon, liver, fetal liver, heart, kidneys, lungs, mammary gland, prostate, salivary glands, muscles, intestines, spinal cord, spleen, stomach, testis, thymus, bronchia, thyroid, and uterus. These 17 genes included 3 KIF genes, KIF1C, KIF3C, and KIF21B, which were the focus in this study.

First, mRNA expression of these genes was examined by RT-PCR (FIG. 1A). mRNA expression of all three genes was detected in four of five glioma cell lines. mRNA expression of all three genes was also detected in PHA-activated T cells (FIG. 1A) and some normal tissues (FIG. 1B). mRNA of the KIF1C gene was more widely expressed than that of the other two KIF genes in the normal tissues. mRNA of the KIF3C gene was detected in the spleen, heart, brain, and testis. mRNA expression of the KIF21B gene was detected in the lung, brain, testis, and thymus.

2.2 Detection of IgG Reactive to the KIF-Derived Peptides

Next, immunogenicity of these three KIFs was examined. Twenty-five peptides derived from 3 KIFs (8 for KIF1C, 11 for KIF3C, and 6 for KIF21B) were prepared based on the binding motifs to the HLA-A24 molecules (Parker K C et al, J Immunol 152: 163-175, 2004) (Table 1).

TABLE 1

KIF-derived peptides binding to the HLA-A24 molecules

|  | Amino acid Peptides sequence | SEQ ID NO. | Length | Binding score |
|---|---|---|---|---|
| KIF1C | 73-82 VYRDIGEEML | 1 | 10 | 240.0 |
|  | 149-157 IYCERVRDL | 2 | 9 | 240.0 |
|  | 149-158 IYCERVRDLL | 3 | 10 | 336.0 |
|  | 331-339 NYEETLSTL | 4 | 9 | 360.0 |
|  | 340-348 RYADRTKQI | 5 | 9 | 120.0 |
|  | 725-734 VYQIPQRRRL | 6 | 10 | 300.0 |
|  | 756-764 CYEVALADF | 7 | 9 | 150.0 |
|  | 968-977 RFVPPHDCKL | 8 | 10 | 79.2 |
| KIF3C | 137-145 QYLVRASYL | 9 | 9 | 300.0 |
|  | 147-155 IYQEEIRDL | 10 | 9 | 360.0 |
|  | 147-156 IYQEEIRDLL | 11 | 10 | 504.0 |
|  | 174-182 VYIKDLSSF | 12 | 9 | 150.0 |
|  | 347-355 SYDESLSTL | 13 | 9 | 240.0 |
|  | 458-467 NYLQEQKERL | 14 | 10 | 300.0 |

TABLE 1-continued

KIF-derived peptides binding to the HLA-A24 molecules

|  | Amino acid Peptides sequence | SEQ ID NO. | Length | Binding score |
|---|---|---|---|---|
|  | 512-520 KYKAMESKL | 15 | 9 | 440.0 |
|  | 607-615 EYIRVRQDL | 16 | 9 | 504.0 |
|  | 629-637 GYLIIENFI | 17 | 9 | 126.0 |
|  | 702-710 RYRAENIMF | 18 | 9 | 200.0 |
|  | 702-711 RYRAENIMFL | 19 | 10 | 400.0 |
| KIF21B | 220-228 GYASTDEEI | 20 | 9 | 55.0 |
|  | 473-482 KYCSHSGLVF | 21 | 10 | 200.0 |
|  | 621-630 HYDGIECLAI | 22 | 10 | 50.0 |
|  | 670-678 AFIPGRPML | 23 | 9 | 36.0 |
|  | 670-679 AFIPGRPMLL | 24 | 10 | 36.0 |
|  | 731-740 NYVPGLTPCL | 25 | 10 | 432.0 |

The binding score was calculated based on the predicted half-time of dissociation from HLA class I molecules as obtained from a web site (Bioinformatics and Molecular Analysis Section, Computed Bioscience and Engineering Laboratory, Division of Computer Research and Technology, NIH).

Next, the abilities of the KIF-derived peptides to be recognized by IgGs of glioma patients were examined, because IgGs reactive to CTL-directed peptides are detectable in the plasma of patients with different types of cancer (Nakatsura T et al, Eur J Immunol 32: 826-836, 2002), along with that levels of IgG well correlated with clinical responses of patients who received peptide vaccination as reported previously (Mine T et al, Clin Cancer Res 10: 929-937, 2004; Yajima N et al, Clin Cancer Res 11: 5900-5911, 2005). IgGs reactive to a corresponding peptide were judged to be significant when the immunofluorescence intensity in 1:100-diluted plasma exceeded 1.25 times that of the control samples with no peptides. These results of the KIF1C peptides are shown in Table 2. Among 8 peptides, 3 KIF1C peptides, $KIF1C_{149-157}$, $KIF1C_{149-158}$, and $KIF1C_{390-348}$, were recognized by IgGs in the plasma of glioma patients more frequently than those of the other 3 peptides. A similar result was observed in the sample of healthy donors. The same assay was performed on 11 KIF3C-derived and 6 KIF21B-derived peptides, and the results are summarized in Table 3. IgGs reactive to 3 KIF3C peptides, $KIF3C_{458-467}$, $KIF3C_{512-520}$, $KIF3C_{702-710}$, and 2 KIF21B peptides, $KIF21B_{220-228}$ and $KIF21B_{621-630}$, were recognized by IgGs in the plasma of glioma patients and healthy donors more frequently than those of the other peptides. Based on these findings, these 8 KIF peptides (3 for KIF1C, 3 for KIF3C, and 2 for KIF21B) were the focus of the following experiments.

TABLE 2

KIF peptide-specific IgG in the plasma of glioma patients and healthy donors

| Subject | KIF1C peptide | | | | | | | | No peptide |
|---|---|---|---|---|---|---|---|---|---|
| | 73-82 | 149-157 | 149-158 | 331-339 | 340-348 | 725-734 | 756-764 | 968-977 | |
| | Immunofluoresence intensity | | | | | | | | |
| Patient | | | | | | | | | |
| 1 | 57.8 | *98.5* | *114.5* | 33.5 | *103.0* | 65.5 | 36.5 | 77.0 | 74.0 |
| 2 | 80.5 | *117.5* | *98.5* | 39.5 | *102.0* | 85.3 | 45.0 | *86.0* | 68.5 |
| 3 | 46.8 | *124.3* | *100.0* | 22.0 | *85.5* | 61.3 | 28.8 | *83.5* | 48.5 |
| 4 | 17.5 | 29.5 | *55.8* | 10.5 | 26.0 | 19.5 | 11.5 | 27.0 | 36.0 |
| 5 | *119.0* | *132.0* | *163.0* | 53.5 | *173.5* | 98.5 | 58.0 | 97.0 | 93.5 |
| 6 | *388.5* | *1066.0* | *706.0* | 86.5 | *595.5* | *385.0* | 185.8 | *533.8* | 155.5 |
| 7 | 68.5 | *108.0* | *105.0* | 35.5 | *103.8* | *134.3* | 40.3 | 74.8 | 66.5 |
| 8 | 11.5 | 12.3 | 16.0 | 8.5 | 14.8 | 10.0 | 6.5 | 12.5 | 30.5 |
| 9 | 11.0 | 27.3 | 19.5 | 5.5 | 17.5 | 9.3 | 7.5 | 19.5 | 28.0 |
| 10 | *1585.0* | *1688.3* | *1264.0* | 485.4 | *2174.5* | *1187.8* | 658.0 | *1132.5* | 640.0 |
| Total | 3/10 | 7/10 | 8/10 | 0/10 | 7/10 | 4/10 | 0/10 | 4/10 | |
| Healthy donor | | | | | | | | | |
| 1 | *122.5* | *122.3* | *213.0* | 70.0 | *141.8* | 99.5 | 87.3 | 117.0 | 97.0 |
| 2 | 19.5 | 31.8 | 41.0 | 13.5 | 21.5 | 19.5 | 14.0 | 23.5 | 36.0 |
| 3 | 64.5 | *113.3* | *112.0* | 29.0 | *74.5* | 66.8 | 46.8 | *76.5* | 55.3 |
| 4 | 29.5 | 47.8 | 55.8 | 16.5 | 45.3 | 30.5 | 20.0 | 33.0 | 49.5 |
| 5 | 50.0 | *87.8* | *245.8* | 35.0 | 59.0 | 52.5 | 40.3 | 58.5 | 61.0 |
| 6 | *97.0* | *134.8* | *189.5* | 40.0 | *156.0* | *87.0* | 47.5 | *94.0* | 69.3 |
| 7 | *648.5* | *468.8* | 442.0 | 233.0 | *1599.0* | *660.0* | 196.0 | *498.5* | 369.5 |
| 8 | *6937.5* | *4962.8* | *4708.0* | 4133.0 | *9638.0* | *4984.0* | 3893.5 | *5813.0* | 3604.5 |
| 9 | *36.5* | *39.5* | *97.5* | 22.5 | *34.0* | *35.3* | 27.0 | 32.3 | 26.5 |
| 10 | *96.5* | *110.3* | *147.5* | 62.5 | *121.5* | *93.8* | 82.0 | *94.0* | 56.3 |
| Total | 6/10 | 8/10 | 7/10 | 0/10 | 7/10 | 5/10 | 1/10 | 5/10 | |

IgG reactive to a corresponding peptide was judged to be significant when the absorbance in a 1:100-dilutated plasma was >1.25 times the absorbance of no peptide control samples. Significance was evaluated for each plasma samples, and the positive results are shown in bold and italics.

TABLE 3

Summary of IgGs reactive to KIF-derived peptides in the plasma of patients and healthy donors

| | Positive cases/total cases | | |
|---|---|---|---|
| Peptides | Patients | Healthy donors | Total |
| KIF1C | | | |
| 73-82 | 3/10 | 6/10 | 9/20 |
| 149-157 | 7/10 | 8/10 | 15/20 |
| 149-158 | 8/10 | 7/10 | 15/20 |
| 331-339 | 0/10 | 0/10 | 0/20 |
| 340-348 | 7/10 | 7/10 | 14/20 |
| 725-734 | 3/10 | 5/10 | 8/20 |
| 756-764 | 0/10 | 1/10 | 1/20 |
| 968-977 | 4/10 | 5/10 | 9/20 |
| KIF3C | | | |
| 137-145 | 2/10 | 1/10 | 3/20 |
| 147-155 | 0/10 | 1/10 | 1/20 |
| 147-156 | 0/10 | 1/10 | 1/20 |
| 174-182 | 1/10 | 2/10 | 3/20 |
| 347-355 | 0/10 | 0/10 | 0/20 |
| 458-467 | 4/10 | 4/10 | 8/20 |
| 512-520 | 5/10 | 4/10 | 9/20 |
| 607-615 | 2/10 | 3/10 | 5/20 |
| 629-637 | 0/10 | 1/10 | 1/20 |
| 702-710 | 7/10 | 9/10 | 16/20 |
| 702-711 | 2/10 | 5/10 | 7/20 |

TABLE 3-continued

Summary of IgGs reactive to KIF-derived peptides in the plasma of patients and healthy donors

| | Positive cases/total cases | | |
|---|---|---|---|
| Peptides | Patients | Healthy donors | Total |
| KIF21B | | | |
| 220-228 | 2/10 | 3/10 | 5/20 |
| 473-482 | 2/10 | 2/10 | 4/20 |
| 621-630 | 2/10 | 5/10 | 7/20 |
| 670-678 | 2/10 | 2/10 | 4/20 |
| 670-679 | 2/10 | 2/10 | 4/20 |
| 731-740 | 1/10 | 1/10 | 2/20 |

2.3 Induction of KIF Peptide Reactive CTLs from the PBMCs of Glioma Patients

Next, it was examined whether or not 8 KIF peptides that were frequently recognized by IgGs in glioma patients possess the potential to induce peptide reactive CTLs from the PBMCs of HLA-A24$^+$ glioma patients. The PBMCs were stimulated in vitro with each of the peptides or control peptides, and examined for their IFN-γ production in response to corresponding peptide-pulsed C1R-A24 cells (Table 4). Successful induction of peptide reactive CTLs was judged to be positive when the P value was less than 0.05 and when the difference in IFN-γ production compared to the control HIV peptide exceeded 100 pg/ml. The positive results are shown in bold and italics. All 8 peptides induced corresponding peptide-reactive CTLs from the PBMCs of 3 or 4 of 10 HLA-A24$^+$ glioma patients. In contrast, only the KIF1C$_{149-158}$ peptide induced peptide-specific CTLs in 1 of 5 HLA-A24$^+$ healthy donors, and the other 7 KIF peptides failed to generate peptide-specific CTLs in any of 5 healthy donors (data not shown).

TABLE 4

Induction of peptide-reactive CTLs from the PBMCs of HLA-A24+ glioma patients or healthy donors

| Subjects Patient | KIF1C | | | KIF3C | | | KIF21B | | EBV | Flu |
|---|---|---|---|---|---|---|---|---|---|---|
| | 149-157 | 149-158 | 340-348 | 458-467 | 512-520 | 702-710 | 220-228 | 621-630 | | |
| | | | | | IFN-γ (pg/ml) | | | | | |
| 1 | 92 | 0 | 66 | 34 | 24 | 11 | 0 | 0 | 0 | 29 |
| 2 | 0 | 11 | 16 | 0 | 0 | 0 | 29 | 10 | 0 | 0 |
| 3 | *224* | 30 | *222* | 30 | 48 | 73 | 56 | 0 | 58 | *167* |
| 4 | 50 | 0 | 80 | *110* | 27 | 0 | *149* | 0 | 0 | 0 |
| 5 | 0 | *123* | *593* | 66 | *345* | *110* | *346* | *194* | 0 | *255* |
| 6 | *121* | *145* | *221* | 55 | 91 | *357* | *170* | *154* | 71 | *137* |
| 7 | *142* | 38 | 65 | *138* | *211* | *243* | 51 | 93 | *142* | 95 |
| 8 | 0 | *203* | 96 | 38 | *285* | 96 | *215* | *198* | 0 | 0 |
| 9 | *162* | 0 | 52 | *162* | 0 | 22 | 0 | 0 | 0 | 0 |
| 10 | 0 | 0 | 0 | 0 | 0 | 0 | 0 | 0 | 0 | 0 |
| Total | 4/10 | 3/10 | 3/10 | 3/10 | 3/10 | 3/10 | 4/10 | 3/10 | 1/10 | 3/10 |

Shown are significant values of P < 0.05 by the two-tailed Student's t-test and difference of 100 pg/ml in IFN-g production compared with the response to the HIV peptide. The positive results are shown in bold and italics.

2.4 Induction of Glioma-Reactive CTLs from HLA-A24+ Glioma Patients

Figure 2:
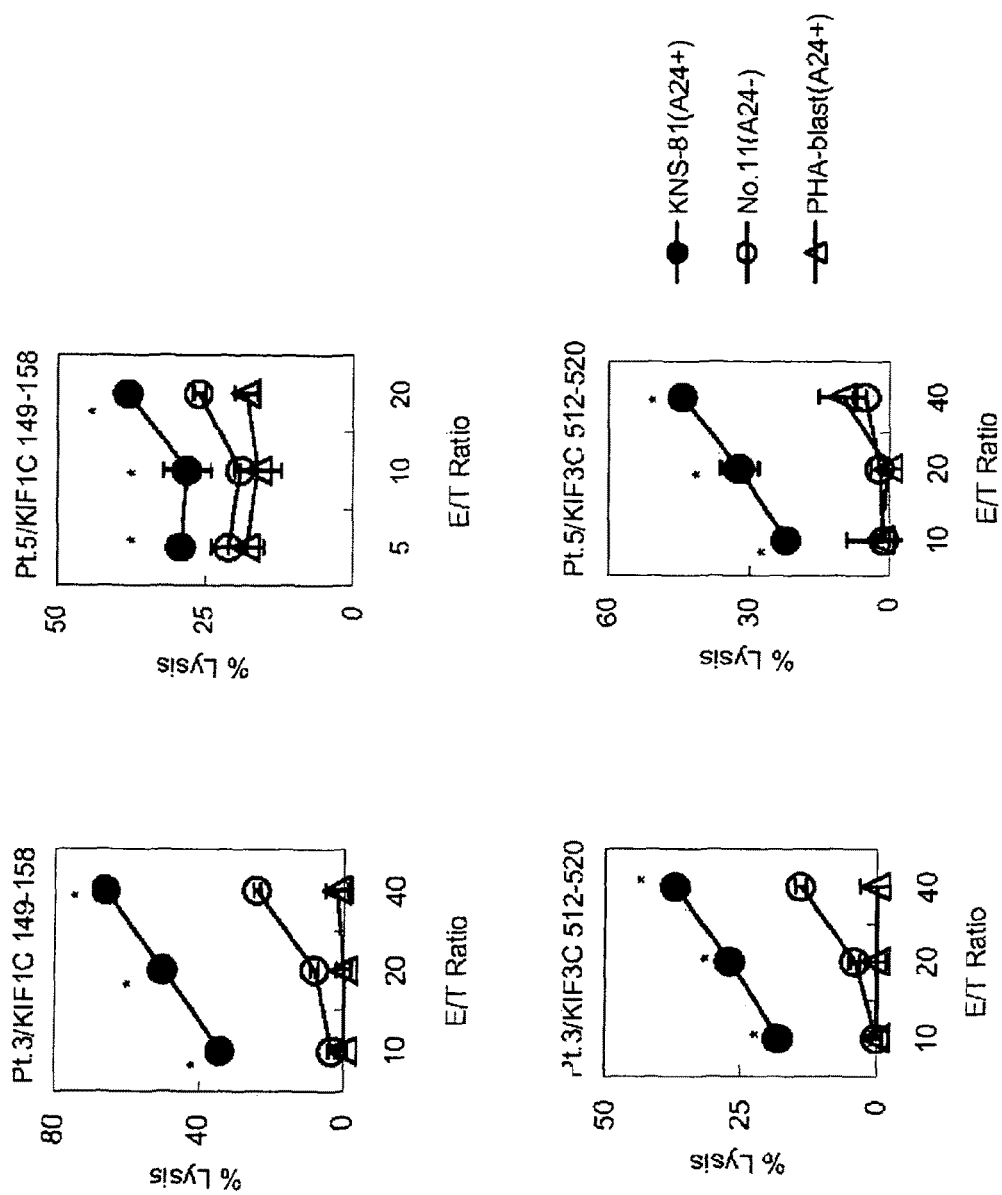
FIG. 2 Induction of glioma-reactive CTLs from HLA-A24$^+$ glioma patients with KIF1C$_{149-158}$ and KIF3C$_{512-520}$ peptides. Cytotoxicity of those peptides against HLA-A24$^+$ KNS-81 cells as well as HLA-A24$^-$ No. 11 cells and HLA-A24$^+$ PHA-blast cells (negative controls) were tested. *P<0.05 in a two-tailed Student's t-test.

It was crucial to determine whether or not these KIF peptides could induce HLA-A24-restricted and glioma-reactive CTLs. To this end, the PBMCs from HLA-A24+ glioma patients were stimulated with each of the 8 KIF peptides, and it was determined whether or not the peptide-reactive CTLs could show cytotoxicity against glioma cells. Among 8 KIF peptides, only the $KIF1C_{149-158}$ and $KIF3C_{512-520}$ peptides efficiently induced glioma-reactive CTLs from the PBMCs of HLA-A24+ glioma patients (FIG. 2). The PBMCs from patients 3 and 5, which were stimulated in vitro with either the $KIF1C_{149-158}$ or $KIF3C_{512-520}$ peptide, exhibited a higher level of cytotoxicity against HLA-A24+ KNS-81 cells than against HLA-A24− No. 11 cells and HLA-A24+ T-cell blasts.

Figure 3:
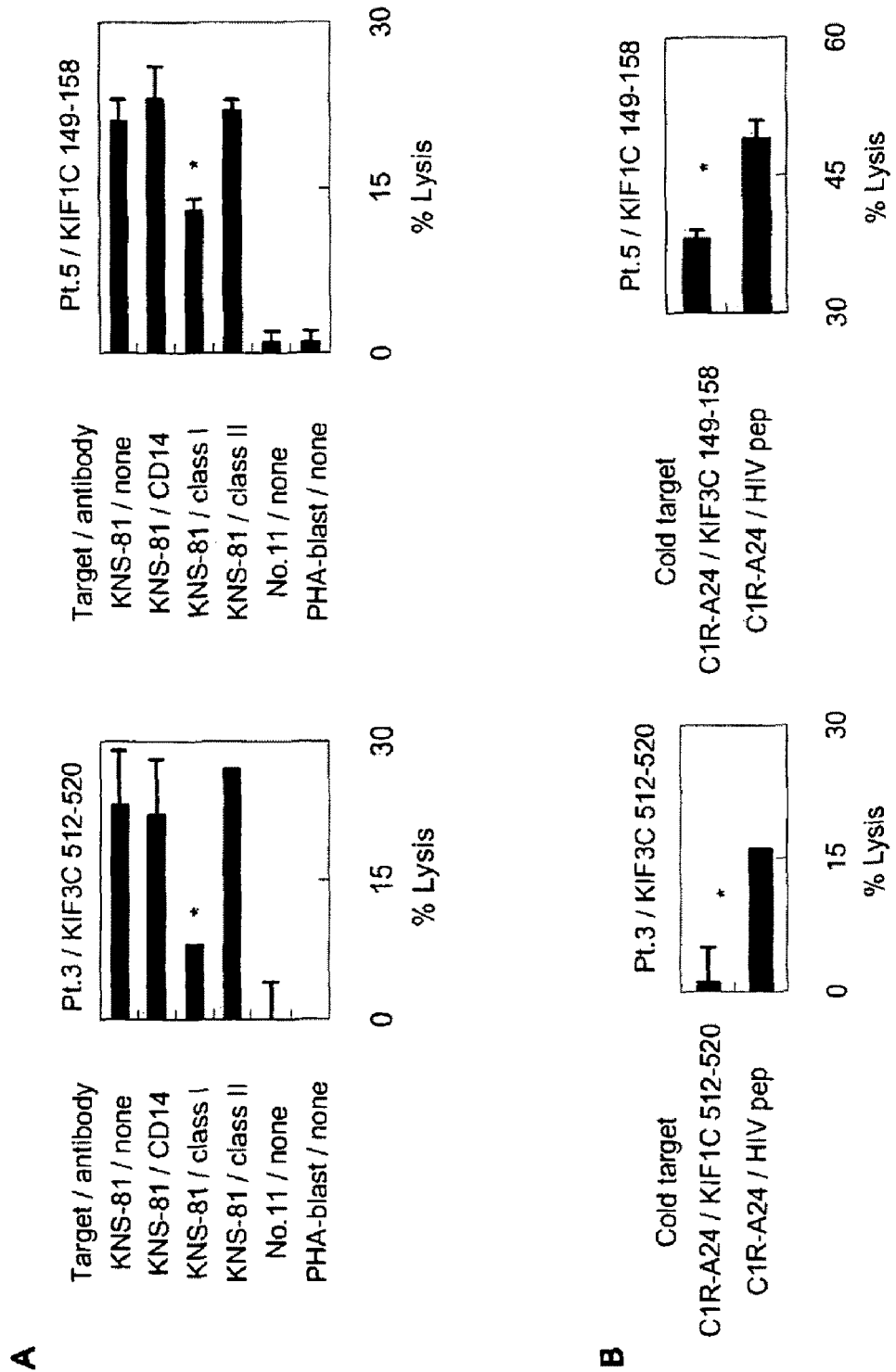
FIG. 3 (A) Inhibition of the cytotoxicity of purified CD8$^+$ T cells from the KIF peptide-stimulated PBMCs against KNS-81 cells using a monoclonal antibody (mAb). *P<0.05 in a two-tailed Student's t-test. (B) Cold inhibition assay for the cytotoxicity of purified CD8$^+$ T cells from the KIF peptide-stimulated PBMCs against KNS-81 cells. *P<0.05 in a two-tailed Student's t-test.

2.5 KIF Peptide-Specific and CD8+ T Cell-Dependent Cytotoxicity Against Glioma Cells Further, identification of the cells responsible for the cytotoxicity of peptide-stimulated PBMCs were examined. Purified CD8+ T cells were used in the following experiments. As shown in FIG. 3A, the cytotoxicity of the $KIF1C_{149-158}$ and $KIF3C_{512-520}$ peptide-induced CD8+ T cells from the HLA-A24+ glioma patients against KNS-81 cells was significantly inhibited by the addition of anti-HLA class I mAb, but not by the addition of anti-HLA class II (HLA-DR) or anti-CD14 mAb as an isotype-matched control. In addition, the cytotoxicity was significantly inhibited by the addition of unlabeled C1R-A24 cells that were pre-pulsed with corresponding KIF peptides, but not by that of HIV peptide-pulsed unlabeled C1R-A24 cells (FIG. 3B). Taken together, the cytotoxicity of the $KIF1C_{149-158}$ and $KIF3C_{512-520}$ peptide-stimulated PBMCs against KNS-81 cells could be ascribed to the corresponding peptide-specific CD8+ T cells.

3. Conclusion

According to the results shown above, KIF-derived peptides, especially $KIF_{149-158}$ and $KIF_{512-520}$ peptides are useful as cancer vaccines for glioma patients.

The invention claimed is:

1. A peptide consisting of the amino acid sequence of SEQ ID NO: 3.

2. A pharmaceutical composition comprising the peptide of claim 1 for treating glioma in HLA-A24 patients having the disease.

3. A method for inducing a HLA-A24 positive glioma-reactive cytotoxic T cell, which comprises contacting peripheral blood mononuclear cells collected from an HLA-A24 positive glioma patient with the peptide of claim 1.

4. A kit for inducing a HLA-A24 positive glioma-reactive cytotoxic T cell, which comprises the peptide of claim 1.

5. A method for preparing an antigen presenting cell on the surface of which a complex between a KIF1C-derived peptide and an HLA-A24 molecule is presented, which comprises incubating a cell having an antigen-presenting ability derived from an HLA-A24 positive glioma patient with the peptide of claim 1.

6. A kit for preparing an antigen presenting cell on the surface of which a complex between a KIF1C-derived peptide and an HLA-A24 molecule is presented, which comprises the peptide of claim 1.

7. A method for the treatment of glioma in a HLA-A24 positive patient, which comprises administering the patient the peptide of claim 1.

8. A method for the treatment of glioma in a HLA-A24 positive patient, which comprises administering the patient an antigen presenting cell on the surface of which a complex between a KIF1C-derived peptide consisting of the amino acid sequence of SEQ ID NO: 8 and an HLA-A24 molecule is presented, wherein said antigen presenting cell has been stimulated ex vivo by incubating the cell in the presence of the peptide.

* * * * *

SEQUENCE LISTING

<160> NUMBER OF SEQ ID NOS: 36

<210> SEQ ID NO 1
<211> LENGTH: 10
<212> TYPE: PRT
<213> ORGANISM: Artificial
<220> FEATURE:
<223> OTHER INFORMATION: Synthetic construct; KIF1C 73-82 peptide

<400> SEQUENCE: 1

Val Tyr Arg Asp Ile Gly Glu Glu Met Leu
1               5                   10

<210> SEQ ID NO 2
<211> LENGTH: 9
<212> TYPE: PRT
<213> ORGANISM: Artificial
<220> FEATURE:
<223> OTHER INFORMATION: Synthetic construct; KIF1C 149-157 peptide

<400> SEQUENCE: 2

Ile Tyr Cys Glu Arg Val Arg Asp Leu
1               5

-continued

```
<210> SEQ ID NO 3
<211> LENGTH: 10
<212> TYPE: PRT
<213> ORGANISM: Artificial
<220> FEATURE:
<223> OTHER INFORMATION: Synthetic construct; KIF1C 149-158 peptide

<400> SEQUENCE: 3

Ile Tyr Cys Glu Arg Val Arg Asp Leu Leu
1               5                   10

<210> SEQ ID NO 4
<211> LENGTH: 9
<212> TYPE: PRT
<213> ORGANISM: Artificial
<220> FEATURE:
<223> OTHER INFORMATION: Synthetic construct; KIF1C 331-339 peptide

<400> SEQUENCE: 4

Asn Tyr Glu Glu Thr Leu Ser Thr Leu
1               5

<210> SEQ ID NO 5
<211> LENGTH: 9
<212> TYPE: PRT
<213> ORGANISM: Artificial
<220> FEATURE:
<223> OTHER INFORMATION: Synthetic construct; KIF1C 340-348 peptide

<400> SEQUENCE: 5

Arg Tyr Ala Asp Arg Thr Lys Gln Ile
1               5

<210> SEQ ID NO 6
<211> LENGTH: 10
<212> TYPE: PRT
<213> ORGANISM: Artificial
<220> FEATURE:
<223> OTHER INFORMATION: Synthetic construct; KIF1C 725-734 peptide

<400> SEQUENCE: 6

Val Tyr Gln Ile Pro Gln Arg Arg Arg Leu
1               5                   10

<210> SEQ ID NO 7
<211> LENGTH: 9
<212> TYPE: PRT
<213> ORGANISM: Artificial
<220> FEATURE:
<223> OTHER INFORMATION: Synthetic construct; KIF1C 756-764 peptide

<400> SEQUENCE: 7

Cys Tyr Glu Val Ala Leu Ala Asp Phe
1               5

<210> SEQ ID NO 8
<211> LENGTH: 10
<212> TYPE: PRT
<213> ORGANISM: Artificial
<220> FEATURE:
<223> OTHER INFORMATION: Synthetic construct; KIF1C 968-977 peptide

<400> SEQUENCE: 8

Arg Phe Val Pro Pro His Asp Cys Lys Leu
1               5                   10
```

-continued

```
<210> SEQ ID NO 9
<211> LENGTH: 9
<212> TYPE: PRT
<213> ORGANISM: Artificial
<220> FEATURE:
<223> OTHER INFORMATION: Synthetic construct; KIF3C 137-145 peptide

<400> SEQUENCE: 9

Gln Tyr Leu Val Arg Ala Ser Tyr Leu
1               5

<210> SEQ ID NO 10
<211> LENGTH: 9
<212> TYPE: PRT
<213> ORGANISM: Artificial
<220> FEATURE:
<223> OTHER INFORMATION: Synthetic construct; KIF3C 147-155 peptide

<400> SEQUENCE: 10

Ile Tyr Gln Glu Glu Ile Arg Asp Leu
1               5

<210> SEQ ID NO 11
<211> LENGTH: 10
<212> TYPE: PRT
<213> ORGANISM: Artificial
<220> FEATURE:
<223> OTHER INFORMATION: Synthetic construct; KIF3C 147-156 peptide

<400> SEQUENCE: 11

Ile Tyr Gln Glu Glu Ile Arg Asp Leu Leu
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic construct; KIF3C 174-182 peptide

<400> SEQUENCE: 12

Val Tyr Ile Lys Asp Leu Ser Ser Phe
1               5

<210> SEQ ID NO 13
<211> LENGTH: 9
<212> TYPE: PRT
<213> ORGANISM: Artificial
<220> FEATURE:
<223> OTHER INFORMATION: Synthetic construct; KIF3C 347-355 peptide

<400> SEQUENCE: 13

Ser Tyr Asp Glu Ser Leu Ser Thr Leu
1               5

<210> SEQ ID NO 14
<211> LENGTH: 10
<212> TYPE: PRT
<213> ORGANISM: Artificial
<220> FEATURE:
<223> OTHER INFORMATION: Synthetic construct; KIF3C 458-467 peptide

<400> SEQUENCE: 14

Asn Tyr Leu Gln Glu Gln Lys Glu Arg Leu
1               5                   10

<210> SEQ ID NO 15
<211> LENGTH: 9
```

```
<212> TYPE: PRT
<213> ORGANISM: Artificial
<220> FEATURE:
<223> OTHER INFORMATION: Synthetic construct; KIF3C 512-520 peptide

<400> SEQUENCE: 15

Lys Tyr Lys Ala Met Glu Ser Lys Leu
1               5

<210> SEQ ID NO 16
<211> LENGTH: 9
<212> TYPE: PRT
<213> ORGANISM: Artificial
<220> FEATURE:
<223> OTHER INFORMATION: Synthetic construct; KIF3C 607-615 peptide

<400> SEQUENCE: 16

Glu Tyr Ile Arg Val Arg Gln Asp Leu
1               5

<210> SEQ ID NO 17
<211> LENGTH: 9
<212> TYPE: PRT
<213> ORGANISM: Artificial
<220> FEATURE:
<223> OTHER INFORMATION: Synthetic construct; KIF3C 629-637 peptide

<400> SEQUENCE: 17

Gly Tyr Leu Ile Ile Glu Asn Phe Ile
1               5

<210> SEQ ID NO 18
<211> LENGTH: 9
<212> TYPE: PRT
<213> ORGANISM: Artificial
<220> FEATURE:
<223> OTHER INFORMATION: Synthetic construct; KIF3C 702-710 peptide

<400> SEQUENCE: 18

Arg Tyr Arg Ala Glu Asn Ile Met Phe
1               5

<210> SEQ ID NO 19
<211> LENGTH: 10
<212> TYPE: PRT
<213> ORGANISM: Artificial
<220> FEATURE:
<223> OTHER INFORMATION: Synthetic construct; KIF3C 702-711 peptide

<400> SEQUENCE: 19

Arg Tyr Arg Ala Glu Asn Ile Met Phe Leu
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic construct; KIF21B 220-228 peptide

<400> SEQUENCE: 20

Gly Tyr Ala Ser Thr Asp Glu Glu Ile
1               5

<210> SEQ ID NO 21
<211> LENGTH: 10
<212> TYPE: PRT
<213> ORGANISM: Artificial
```

```
<220> FEATURE:
<223> OTHER INFORMATION: Synthetic construct; KIF21B 473-482 peptide

<400> SEQUENCE: 21

Lys Tyr Cys Ser His Ser Gly Leu Val Phe
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic construct; KIF21B 621-630 peptide

<400> SEQUENCE: 22

His Tyr Asp Gly Ile Glu Cys Leu Ala Ile
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic construct; KIF21B 670-678 peptide

<400> SEQUENCE: 23

Ala Phe Ile Pro Gly Arg Pro Met Leu
1               5

<210> SEQ ID NO 24
<211> LENGTH: 10
<212> TYPE: PRT
<213> ORGANISM: Artificial
<220> FEATURE:
<223> OTHER INFORMATION: Synthetic construct; KIF21B 670-679 peptide

<400> SEQUENCE: 24

Ala Phe Ile Pro Gly Arg Pro Met Leu Leu
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic construct; KIF21B 731-740 peptide

<400> SEQUENCE: 25

Asn Tyr Val Pro Gly Leu Thr Pro Cys Leu
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic construct; Flu virus-derived peptide

<400> SEQUENCE: 26

Arg Phe Tyr Ile Gln Met Cys Thr Glu Leu
1               5                   10

<210> SEQ ID NO 27
<211> LENGTH: 9
<212> TYPE: PRT
<213> ORGANISM: Artificial
<220> FEATURE:
<223> OTHER INFORMATION: Synthetic construct; EB virus-derived peptide
```

```
<400> SEQUENCE: 27

Thr Tyr Gly Pro Val Phe Met Cys Leu
1               5

<210> SEQ ID NO 28
<211> LENGTH: 10
<212> TYPE: PRT
<213> ORGANISM: Artificial
<220> FEATURE:
<223> OTHER INFORMATION: Synthetic construct; HIV-derived peptide

<400> SEQUENCE: 28

Arg Tyr Leu Arg Gln Gln Leu Leu Gly Ile
1               5                   10

<210> SEQ ID NO 29
<211> LENGTH: 20
<212> TYPE: DNA
<213> ORGANISM: Artificial
<220> FEATURE:
<223> OTHER INFORMATION: Synthetic construct; Primer

<400> SEQUENCE: 29
caagtgtgtg gtcagcatgc                                           20

<210> SEQ ID NO 30
<211> LENGTH: 19
<212> TYPE: DNA
<213> ORGANISM: Artificial
<220> FEATURE:
<223> OTHER INFORMATION: Synthetic construct; Primer

<400> SEQUENCE: 30
ctctggttct cactaagcg                                            19

<210> SEQ ID NO 31
<211> LENGTH: 19
<212> TYPE: DNA
<213> ORGANISM: Artificial
<220> FEATURE:
<223> OTHER INFORMATION: Synthetic construct; Primer

<400> SEQUENCE: 31
tatgatgcca gctccaagc                                            19

<210> SEQ ID NO 32
<211> LENGTH: 20
<212> TYPE: DNA
<213> ORGANISM: Artificial
<220> FEATURE:
<223> OTHER INFORMATION: Synthetic construct; Primer

<400> SEQUENCE: 32
attcttggtg acgaaggagg                                           20

<210> SEQ ID NO 33
<211> LENGTH: 20
<212> TYPE: DNA
<213> ORGANISM: Artificial
<220> FEATURE:
<223> OTHER INFORMATION: Synthetic construct; Primer

<400> SEQUENCE: 33
aatgtgatca gcgccttagg                                           20
```

```
<210> SEQ ID NO 34
<211> LENGTH: 20
<212> TYPE: DNA
<213> ORGANISM: Artificial
<220> FEATURE:
<223> OTHER INFORMATION: Synthetic construct; Primer

<400> SEQUENCE: 34
tgtagcatgg cattctctcg                                                   20

<210> SEQ ID NO 35
<211> LENGTH: 18
<212> TYPE: DNA
<213> ORGANISM: Artificial
<220> FEATURE:
<223> OTHER INFORMATION: Synthetic construct; Primer

<400> SEQUENCE: 35
cttcgcgggc gacgatgc                                                     18

<210> SEQ ID NO 36
<211> LENGTH: 20
<212> TYPE: DNA
<213> ORGANISM: Artificial
<220> FEATURE:
<223> OTHER INFORMATION: Synthetic construct; Primer

<400> SEQUENCE: 36
cgtacatggc tggggtgttg                                                   20
```